United States Patent
Bender et al.

(10) Patent No.: US 10,688,104 B2
(45) Date of Patent: Jun. 23, 2020

(54) COMBINATION THERAPY WITH NOTCH AND PD-1 OR PD-L1 INHIBITORS

(71) Applicant: Eli Lilly and Company, Indianapolis, IN (US)

(72) Inventors: Mark Harrath Bender, Indianapolis, IN (US); Hong Gao, Indianapolis, IN (US); Bharvin Kumar Patel, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/301,360

(22) PCT Filed: May 16, 2017

(86) PCT No.: PCT/US2017/032790
§ 371 (c)(1),
(2) Date: Nov. 13, 2018

(87) PCT Pub. No.: WO2017/200969
PCT Pub. Date: Nov. 23, 2017

(65) Prior Publication Data
US 2019/0192531 A1 Jun. 27, 2019

Related U.S. Application Data

(60) Provisional application No. 62/339,363, filed on May 20, 2016.

(51) Int. Cl.
| | | |
|---|---|---|
| A61K 31/55 | (2006.01) | |
| A61K 39/395 | (2006.01) | |
| C07K 16/28 | (2006.01) | |
| A61K 31/542 | (2006.01) | |
| A61K 45/06 | (2006.01) | |
| A61P 35/00 | (2006.01) | |
| A61K 39/00 | (2006.01) | |

(52) U.S. Cl.
CPC .......... *A61K 31/55* (2013.01); *A61K 31/542* (2013.01); *A61K 39/3955* (2013.01); *A61K 45/06* (2013.01); *A61P 35/00* (2018.01); *C07K 16/2818* (2013.01); *C07K 16/2827* (2013.01); *A61K 2039/505* (2013.01); *C07K 2317/21* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,943,743 B2 | 5/2011 | Korman et al. | |
| 8,008,449 B2 | 8/2011 | Korman et al. | |
| 8,354,509 B2 | 1/2013 | Carven et al. | |
| 8,569,286 B2 | 10/2013 | Hipskind et al. | |
| 8,609,089 B2 | 12/2013 | Langermann et al. | |
| 2005/0187179 A1 | 8/2005 | Miele et al. | |
| 2010/0028330 A1 | 2/2010 | Collins et al. | |
| 2010/0203056 A1 | 8/2010 | Irving et al. | |
| 2012/0039906 A1 | 2/2012 | Olive et al. | |
| 2012/0114649 A1 | 5/2012 | Langermann et al. | |
| 2013/0029972 A1 | 1/2013 | Hipskind | |
| 2018/0104254 A1 | 4/2018 | Karim et al. | |
| 2019/0209581 A1 | 7/2019 | Benhadji et al. | |

FOREIGN PATENT DOCUMENTS

| | | |
|---|---|---|
| WO | WO 1998/28268 | 7/1998 |
| WO | WO 2006/121168 | 11/2006 |
| WO | 2007005874 | * 1/2007 |
| WO | WO 2007/005874 | 1/2007 |
| WO | WO 2009/114335 | 9/2009 |
| WO | WO 2010/075074 | 7/2010 |
| WO | WO 2010/077634 | 7/2010 |
| WO | WO 2011/060051 | 5/2011 |

(Continued)

OTHER PUBLICATIONS

"Chemotherapy of Neoplastic Diseases" in Goodmann & Gilman's Manual of Pharmacology and Therapeutics, 2008, McGraw-Hill Medical 2008 (Year: 2008).*
Lipson et al., Clin Cancer Res. Jan. 15, 2013; 19(2): 462-468 (Year: 2013).*
Pardoll, Nature Reviews Cancer vol. 12, pp. 252-264 (2012) (Year: 2012).*
Mathieu et al., Immunology and CII Biology {2013) 91, 82-88 (Year: 2013).*
Seow et al., OncoTargets and Therapy 2016:9 1899-1920 (Year: 2016).*
U.S. Appl. No. 16/093,117, filed Oct. 11, 2018, by Patel et al.
U.S. Appl. No. 16/093,123, filed Oct. 11, 2018, by Beckmann et al.

(Continued)

*Primary Examiner* — Karl J Puttlitz
(74) *Attorney, Agent, or Firm* — Morrison & Foerster LLP

(57) ABSTRACT

The present invention provides medicaments for use in treating and methods of treating T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, Sung cancer, non small-cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, or adenoid cystic carcinoma in a patient comprising combination therapy with 4,4,4-trifluoro-N-[(1S)-2~[[(7S)-5-(2-hydroxyemyl)-6-oxo-7H-pyrido[23-d][3]benzazepin-7-yl]amino]-1-methyl-2-oxo-ethyl}butanamide, or a pharmaceutically acceptable salt or hydrate thereof, and a PD-1 or a PD-L1 inhibitor selected from pembrolizumab, nivolumab, atezolizumab, durvalumab, and avelumab.

9 Claims, No Drawings

(56) References Cited

FOREIGN PATENT DOCUMENTS

| WO | WO 2011/066389 | | 6/2011 |
|---|---|---|---|
| WO | WO 2012/097039 | | 7/2012 |
| WO | 2013016081 | * | 1/2013 |
| WO | WO 2013/016081 | | 1/2013 |
| WO | WO 2013/079174 | | 6/2013 |
| WO | WO 2015/193352 | | 12/2015 |
| WO | WO 2016/164580 | | 10/2016 |
| WO | WO 2016/168014 | | 10/2016 |
| WO | WO 2018/201056 | | 11/2018 |

OTHER PUBLICATIONS

Anonymous, "FS25 Peripheral T-Cell Lymphoma Facts I page 1 Revised," Leukemia & Lymphoma Society (2014) Retrieved on https://www.lls.org/sites/default/files/file_assets/peripheraltcell-lymphomafacts.pdf.

Anonymous, "Notch Inhibitor Shows Modest Efficacy," Cancer Discovery (2016) pp. 1-3. Retrieved on URL:http://cancerdiscovery.aacrjournals.org/content/early/2016/12/13/2159-8290.CD-NB2016-159.

Bell et al., "Expression and significance of Notch signaling pathway in salivary adenoid cystic carcinoma," Annals of Diagnostic Pathology, (2014) 18: 10-13.

Belyea et al, "Inhibition of the Notch-Hey1 Axis Blocks Embryonal Rhabdomyosarcoma Tumorigenesis," Clin Cancer Res, (2011) 17(23): 7324-7336.

Bender et al., "Novel inhibitor of Notch signaling for the treatment of cancer" (2013) Cancer Res 73(8 Supplement):1131.

Chou et al, "Quantitative analysis of dose-effect relationships: the combined effects of multiple drugs or enzyme inhibitors," Adv. Enzyme Regul., (1984) 22: 27-55.

Clinical Trial Identifier NCT02079636. Updated Feb. 3, 2016. Retrieved from https://clinicaltrials.gov/archive/NCT02079636/2016_02_03.

Clinical Trial Identifier NCT02784795. "A Study of LY3039478 in Participants with Advanced or Metastatic Solid Tumors". Updated May 26, 2016. Retrieved from https://clinicaltrials.gov/archive/NCT02784795/2016_05_26.

Cullion et al., "Targeting the Notch1 and mTOR pathways in a mouse T-ALL model," Blood (2009) 113:6172-6181.

Database WPI, Week 201156, Thomas Scientific, London, GB; AN 2011-J01934, XP002771616, CN 102 085 372 (Inst Basic Medical Sci Chinese Acad Medi), Jun. 8, 2011 abstract.

Eisenhauer et al., "New response evaluation criteria in solid tumours: revised RECIST guideline (version 1.1)," European Journal of Cancer, (2009) 45: 228-247.

Gadducci et al., "Pharmacological treatment for uterine leiomyosarcomas", Expert Opin Pharmacother (2014) 16(3):335-346.

Gast et al., "Somatic alterations in the melanoma genome: A high-resolution array-based comparative genomic hybridization study," Genes, Chromosomes & Cancer, (2010) 49: 733-745.

Grabher et al., "Notch 1 activation in the molecular pathogenesis of T-cell acute lymphoblastic leukaemia," Nature Review Cancer, (2006) (6):347-359.

Hamid, O. et al., "Safety and Tumor Responses with Lambrolizumab (Anti-PD-1) in Melanoma," New England Journal of Medicine, (2013) 369(2): 134-44.

Hill et al., "Gamma secretase inhibition increase recognition of multiple myeloma by BCMA-specific chimeric antigen receptor modified T cells," J Immunotherapy of Cancer (2017) 5(S2):5-6.

Holford et al., "Understanding the Dose-Effect Relationship," Clin Pharmacokinet.(1981) 6: 429-453.

Lipson et al., "Durable Cancer Regression Off-treatment and Effective Reinduction Therapy with an Anti-PD-1 Antibody," Clin Cancer Res (2013) 19(2):462-468.

Loewe et al., "Effect of combinations: Mathematical basis of problem," Arch. Exp. Pathol. Pharmacol., (1926) 114: 313-326.

Massard et al., "First-in-human study of LY3039478, a Notch signaling inhibitor in advanced or metastatic cancer," J Clin Oncol (2015) 33(15_suppl):2533.

Mathieu et al., "Notch signaling regulates PD-1 expression during CD8+ T-cell activation," Immunology and Cell Biology, (2013) 91: 82-88.

Meng et al., "Association of Notch signaling pathway expression in liposarcomas with outcome, and targeting with gamma-secretase inhibitors," J Clin Oncol (2009) 27(15 Supp):10526.

Nakahara et al., "Hes1 immortalizes committed progenitors and plays a role in blast crisis transition in chronic myelogenous leukemia," Blood, (2010) 115(14): 2872-2881.

Park et al., "Notch3 Gene Amplification in Ovarian Cancer," Cancer Research, (2006) 66: 6312-6318.

Ranganathan et al., "Notch signalling in solid tumours: a little bit of everything but not all the time," Nature Review Cancer, (2011) 11:338-351.

Ravi et al., "Identification of therapeutic targets in angiosarcoma," J Clin Incol (2007) 25(18 Supp):10030.

Robert-Moreno et al., "The notch pathway positively regulates programmed cell death during erythroid differentiation," Leukemia, (2007) 21: 1496-1503.

Roma et al., "Notch Pathway Inhibition Significantly Reduces Rhabdomyosarcoma Invasiveness and Mobility In Vitro," Clin Cancer Res, (2011) 17(3): 505-513.

Rosati et al, "Constitutively activated Notch signaling is involved in survival and apoptosis resistance of B-CLL cells," Blood, (2009) 113: 856-865.

Sekiya et al., "Intrahepatic cholangiocarcinoma can arise from Notch-mediated conversion of hepatocytes," J Clin Invest, (2012) 122(11): 3914-3918.

Sliwa et al. "Hyperexpression of NOTCH-1 is found in immature acute myeloid leukemia." Int J Clin Exp Pathol, (2014) 7(3): 882-889.

Smith et al., "A phase I dose escalation and expansion study of the anticancer stem cell agent demcizumab (Anti-DLL4) in patients with previously treated solid tumors," Clin Cancer Re (2014) 20(24):6295-303.

Stoeck et al., "Discovery of Biomarkers Predictive of GSI Response in Triple-Negative Breast Cancer and Adenoid Cystic Carcinoma," Cancer Discovery, (2014) 4: 1154-1167.

Takebe et al., "Targeting Notch signaling pathway in cancer: Clinical development advances and challenges," Pharmacol Ther (2014) 141(2):140-149.

Tejada et al., "The challenge of targeting Notch in hematologic malignancies," Frontiers in Pediatrics (2014) 2:1-8.

Villanueva et al., "Notch Signaling is Activated in Human Hepatocellular Carcinoma and Induces Tumor Formation in Mice," Gastroenterology, (2012) 143: 1660-1669.

Wang et al., "Hedgehog and Notch Signaling Regulate Self-Renewal of Undifferentiated Pleomorphic Sarcomas," Cancer Res, (2012) 72: 1013-1022.

Weng et al., "Activating mutations of NOTCH1 in human T cell acute lymphoblastic leukemia," Science, (2004) 306(5694):269-271.

Westhoff et al., "Alterations of the Notch pathway in lung cancer," PNAS, (2009) 106: 22293-22298.

Worcester, "GSI inhibition may boost BCMA CAR T-cell therapy efficacy in myeloma," Hematology News. Published on Nov. 27, 2017. Retrieved on https://www.mdedge.com/hematology-oncology/article/152733/multiple-myeloma/gsi-inhibition-may-boost-bcma-car-t-cell-therapy.

Wu et al., "Clinicopathological significance of aberrant Notch receptors in intrahepatic cholangiocarcinoma," Int J Exp Pathol, (2014) 7(6): 3272-3279.

Yoon et al., "Clinicopathological significance of altered Notch signaling in extrahepatic cholangiocarcinoma and gallbladder carcinoma," World J Gastroenterol, (2011) 17(35): 4023-4030.

Yuen et al., "Abstract CT048: Population pharmacokinetics and pharmacodynamics for an oral Notch inhibitor, LY3039478, in the first-in-man study," Cancer Research (2016) 76(14):CT048.

(56) References Cited

OTHER PUBLICATIONS

Martin-Liberal, "Leiomyosarcoma: Principles of management, intractable & rare disease research," (2013) 2(4):127-129.

* cited by examiner

COMBINATION THERAPY WITH NOTCH AND PD-1 OR PD-L1 INHIBITORS

CROSS REFERENCE TO RELATED APPLICATIONS

This application is a U.S. National Stage Application under 35 U.S.C. § 371 of International Application No. PCT/US2017/032790, filed internationally on May 16, 2017, which claims priority to and the benefit of U.S. Provisional Application No. 62/339,363 filed May 20, 2016, the entire contents of which are incorporated herein by reference in their entirety.

The present invention relates to cancer therapy with 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof (Compound A) and a Programmed Death Receptor 1 (PD-1) inhibitor, or a Programmed Death Receptor Ligand 1 (PD-L1) inhibitor and to methods of using combinations to treat cancer.

4,4,4-trifluoro-N-[(1S)-2-[[(7S)-5-(2-hydroxyethyl)-6-oxo-7H-pyrido[2,3-d][3]benzazepin-7-yl]amino]-1-methy-2-oxo-ethyl]butanamide, or a pharmaceutically acceptable salt or hydrate thereof, is a Notch pathway signaling inhibitor compound. Notch signaling plays an important role during development and tissue homeostasis. Dysregulation of Notch signaling due to mutation, amplification, or overexpression of ligands and/or receptors, is implicated in a number of malignancies. Inhibition of Notch signaling is a potential target for the development of cancer therapeutics. Compound A and methods of making and using this compound, including for the treatment of T-cell acute lymphoblastic leukemia, acute lymphoblastic leukemia, acute myelogenous leukemia, chronic myelogenous leukemia, erythroleukemia, breast cancer, ovarian cancer, melanoma, lung cancer, pancreatic cancer, glioblastoma, colorectal cancer, head and neck cancer, cervical cancer, prostate cancer, liver cancer, squamous cell carcinoma (oral), skin cancer and medulloblastoma are disclosed in WO 2013/016081, and for treating leiomyosarcoma in PCT/US2016/026119. Compound A is being investigated in a phase 1 clinical trial and expansion cohorts having a defined molecular pathway alteration, or a tissue based malignant tumor, and in combination with other specifically identified anticancer agents against specified tumor types showing mutations, amplification, or gene expression alterations related to Notch pathway signaling, and in a clinical trial in patients with T-cell acute lymphoblastic leukemia or T-cell lymphoblastic lymphoma (T-ALL/T-LBL).

Tumor cells escape detection and elimination by the immune system through various mechanisms. Endogenously, immune checkpoint pathways are used in maintenance of self-tolerance and control of T cell activation. Binding of the PD-1 ligands, PD-L1 and PD-L2, to the PD-1 receptor found on T cells, inhibits T cell proliferation and cytokine production. Upregulation of PD-1 ligands occurs in some tumors and signaling through this pathway contributes to inhibition of active T-cell immune surveillance of tumors. Inhibition of PD-1 or PD-L1, has been shown to restore immune mediated destruction of tumors. Clinical research has found that targeting PD-1 or PD-L1 with antagonist antibodies releases the PD-1 pathway mediated inhibition of the immune response, including the anti-tumor response.

Notch pathway signaling is reported to be a regulator of PD-1 expression by activated $CD8^+$ T cells, Mathieu et al, *Immunology and Cell Biology*, 2013, 91: 82-88, Despite existing treatment options for patients with cancer, there continues to be a need for new and different therapies affording one or both of enhanced efficacy and lower toxicity. Current immunotherapies have shown a benefit in a subset of cancer types and only in a subset of patients. Novel therapies or combination strategies are needed to improve the overall response against specific cancers or to facilitate extension of these treatments into cancers that may currently be less responsive to either agent alone.

It is believed the present invention provides beneficial therapeutic effects from the combined activity of Compound A and anti-PD-1 or PD-L1 monoclonal antibody inhibitor activity against T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small-cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumors, soft tissue sarcoma, and adenoid cystic carcinoma as compared to the therapeutic effects provided by either agent alone.

One aspect of the present invention provides a method of treating T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, or adenoid cystic carcinoma in a patient comprising administering to a patient in need of treatment an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of a PD-1 or PD-L1 inhibitor selected from pembrolizumab, nivolumab, atezolizumab, durvalumab, and avelumab.

A further aspect of the present invention provides a method of treating colorectal cancer in a patient, comprising administering to the patient in need of treatment an effective amount of 4,4,4-trifluoro-N-[(1S)-2-[[(7S)-5-(2-hydroxyethyl)-6-oxo-7H-pyrido pyrido[2,3-d][3]benzazepin-7-yl]amino]-1-methyl-2-oxo-ethyl]butanamide, or a pharmaceutically acceptable salt or hydrate thereof, and an effective amount of a PD-1 or PD-L1 inhibitor selected from pembrolizumab, nivolumab, atezolizumab, durvalumab, and avelumab.

Another aspect of the present invention provides a method of treating T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, or adenoid cystic carcinoma in a patient, comprising administering to a patient in need of treatment, simultaneously, separately, or sequentially, an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of a PD-1 or PD-L1 inhibitor selected from pembrolizumab, nivolumab, atezolizumab, durvalumab, and avelumab. Another aspect of the present invention provides a method of treating colorectal cancer in a patient, comprising administering to a patient in need of treatment, simultaneously, separately, or sequentially, an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of a PD-1 or PD-L1 inhibitor selected from pembrolizumab, nivolumab, atezolizumab, durvalumab, and avelumab.

A further aspect of the present invention provides a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof; and a PD-1 or PD-L1 inhibitor selected from pembrolizumab, nivolumab, atezolizumab, durvalumab, and avelumab; for simultaneous, separate, or sequential use in the treatment of T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, or adenoid cystic carcinoma.

Another aspect of the present invention provides a compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof; and a PD-1 or PD-L1 inhibitor selected from pembrolizumab, nivolumab, atezolizumab, durvalumab, and avelumab; for simultaneous, separate, or sequential use in the treatment of colorectal cancer.

A further aspect of the present invention provides: use of 4,4,4-trifluoro-N-[(1S)-2[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof for the manufacture of a medicament; and use of a PD-1 or PD-L1 inhibitor selected from pembrolizumab, nivolumab, atezolizumab, durvalumab, and avelumab for the manufacture of a medicament; for the simultaneous, separate, or sequential treatment of T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, or adenoid cystic carcinoma.

A further aspect of the present invention provides: use of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof for the manufacture of a medicament; and use of a PD-1 or PD-L1 inhibitor selected from pembrolizumab, nivolumab, atezolizumab, durvalumab, and avelumab for the manufacture of a medicament; for the simultaneous, separate, or sequential treatment of colorectal cancer.

Another aspect of the present invention is a commercial package comprising a separate composition of each of the therapeutic agents together with instructions for simultaneous, separate or sequential administration for use in treating T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, or adenoid cystic carcinoma.

A still further aspect of the present invention is a commercial package comprising a separate composition of each of the therapeutic agents together with instructions for simultaneous, separate or sequential administration for use in treating colorectal cancer.

The compound 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, (Compound A) has the CAS registry number 142138-81-4. Alternatively, the compound may be named: N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluorobutanamide. Other names may be used to unambiguously identify Compound A.

The terms, as used herein, "PD-1 inhibitor" and "PD-L1 inhibitor" mean a fully human, or humanized IgG optionally optimized, monoclonal antibody.

PD-1 inhibitors include nivolumab and pembrolizumab. Nivolumah, (Opdivo®) also known as iMDX-1106, MDX-1106-04, ONO-4538, or BMS-936558 and has a CAS Registry Number: of 946414-94-4. Nivolumab is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pembrolizumab, (Keytruda®) (formerly lambrolizumab), also known as Merck 3745, MK-3475 or SCH-900475, is a humanized IgG4 monoclonal antibody that binds to PD-1. Pembrolizumab is disclosed in Hamid, O. et al., *New England Journal of Medicine*, 2013, 369(2): 134-44; WO2009/114335; and U.S. Pat. No. 8,354,509. Other anti-PD-1 antibodies are disclosed in U.S. Pat. No. 8,609,089; US 2010028330; and/or US 20120114649.

PD-L1 inhibitors include YW243.55.S70, MPDL3280A, MEDI-4736, MSB-0010718C, and MDX-1105. YW243.55.S70 is an anti-PD-L1 antibody described in WO2010/077634 and US20100203056. MDPL3280A (also known as RG7446, RO5541267, atezolizumah, Tecentriq™) is a fully humanized Fc optimized IgG1 monoclonal antibody that binds to PD-L1. MPDL3280A and other human monoclonal antibodies to PD-L1 are disclosed in U.S. Pat. No. 7,943,743 and US 20120039906. MEDI-4736 (also known as durvalumab) is an Fc optimized IgG1 monoclonal antibody to PD-L1 and is described in WO2011/066389. MSB-0010718C (also known as avelumab) is a fully human IgG1 monoclonal antibody to PD-L1 and is described in WO2013/079174. MDX-1105, also known as BMS-936559, is a fully human IgG4 monoclonal anti-PD-L1 antibody described in WO2007/005874.

As used herein, the term "patient" refers to a mammal, preferably a human.

"Therapeutically effective amount" or "effective amount" means the dosage of Compound A, or pharmaceutically acceptable salt or hydrate thereof, or pharmaceutical composition containing Compound A, or pharmaceutically acceptable salt or hydrate thereof, and the dosage of a PD-1 or PD)-L1 inhibitor, or pharmaceutical composition containing a PD-1 or PD-L1 inhibitor necessary to inhibit tumor cell growth and eliminate or slow or arrest the progression of the cancer in a patient. Dosages of Compound A, or a pharmaceutically acceptable salt or hydrate thereof, are in the range of 2.5 mg/patient to 75 mg/patient once per day every other day over a five day period followed by two days without dosing (T.I.W.). Dosages of a PD-1 or PD-L1 inhibitor, unless otherwise specified on the label, are in the range of 1-3 mg/kg intravenous infusion over 30 to 60 minutes once every 14-21 days. Preferred dosages of Compound A, or a pharmaceutically acceptable salt or hydrate thereof, are in the range of 10 mg to 50 mg T.I.W. The exact dosage required to treat a patient and the length of treatment time will be determined by a physician in view of the stage and severity of the disease as well as the specific needs and response of the individual patient. The dosing administration may be adjusted to provide a more optimal therapeutic benefit to a patient and to manage or ameliorate any drug related toxicities. Alternative dosing schedules such as once per day (QD), twice per day (B.I.D.), three times a day (T.I.D.); dosing once per day every other day (Q2D); or every third day (Q3D) may be appropriate for Compound A. Dosing administration for PD-1 or PD-L1 inhibitors may be adjusted, including withholding a dose or permanently discontinuing further dosing to manage or ameliorate drug related toxicities.

A combination therapy of the present invention is carried out by administering to a T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, and adenoid cystic carcinoma preferably a soft tissue sarcoma patient requiring treatment, an effective amount of Compound A, or a pharmaceutically acceptable salt or hydrate thereof, once per day every other day over five days and two days without dosing each week (7-days) over a 28 day cycle and a PD-1 or PD-L1 inhibitor at 1-3 mg/kg over 30-60 minutes once every 14-21 days.

The terms "treatment," "treat," and "treating," are meant to include the full spectrum of intervention for the cancer from which the patient is suffering, such as administration of Compound A and A PD-1 or PD-L1 inhibitor to alleviate, slow, stop, or reverse one or more of the symptoms and to delay, stop, or reverse progression of the cancer even if the cancer is not actually eliminated.

Compound A or a pharmaceutically acceptable salt or hydrate thereof, is preferably formulated as a pharmaceutical composition using a pharmaceutically acceptable carrier and administered by a variety of routes. Preferably, such compositions are for oral administration. A PD-1 or PD-L1 inhibitor is preferably formulated as a pharmaceutical composition using a pharmaceutically acceptable carrier and administered by a parenteral route, preferably intravenous infusion. Preferably, such compositions may be a lyophilized powder or a liquid composition. Reconstitution or dilution to ready for administration dosages are according to label or by routine skill in the art. Such pharmaceutical compositions and processes for preparing them are well known in the art. See, for example, HANDBOOK OF PHARMACEUTICAL EXCIPIENTS, 5$^{th}$ edition, Rowe et al., Eds., Pharmaceutical Press (2006); and REMINGTON: THE SCIENCE AND PRACTICE OF PHARMACY (Troy, et al., Eds., 21" edition, Lippincott Williams & Wilkins (2006).

Compound A is capable of reaction with a number of inorganic and organic counterions to form pharmaceutically acceptable salts. Such pharmaceutically acceptable salts and common methodology for preparing them are well known in the art. See, for example, P. Stahl, et al., HANDBOOK OF PHARMACEUTICAL SALTS: PROPERTIES, SELECTION AND USE, (VCEA/Wiley-Val, 2002); S. M. Berge, et al., "Pharmaceutical Salts," *Journal of Pharmaceutical Sciences*, Vol. 66, No. 1, January 1977.

The efficacy of the combination treatment of the invention can be measured by various endpoints commonly used in evaluating cancer treatments, including but not limited to, tumor regression, tumor weight or size shrinkage, time to progression, overall survival, progression free survival, overall response rate, duration of response, inhibition of metastatic spread without tumor regression, and PET/CT imaging.

The terms "combination," "therapeutic combination" and "pharmaceutical combination" refer to a non-fixed dose combination, optionally packaged together with instructions for combined administration where the individual therapeutic agents, Compound A, or a pharmaceutically acceptable salt or hydrate thereof, and a PD-1 or PD-L1 inhibitor may be administered independently at the same time or separately within time intervals that allow the therapeutic agents to exert a cooperative effect.

The term "simultaneous" administration means the administration of each of Compound A and a PD-1 or PD-L1 inhibitor to a patient in a single action such as where each of Compound A and a PD-1 or PD-L1 inhibitor are administered independently at substantially the same time or separately within time intervals that allow Compounds A and a PD-1 or PD-L1 inhibitor to show a cooperative therapeutic effect.

The term "separate" administration means the administration of each of Compound A and a PD-1 or PD-L1 inhibitor to a patient from non-fixed dose dosage forms simultaneously, substantially concurrently, or sequentially in any order. There may, or may not, be a specified time interval for administration of each Compound A and a PD-1 or PD-L1 inhibitor.

The term "sequential" administration means the administration of each of Compound A and a PD-1 or PD-L1 inhibitor to a patient from non-fixed (separate) dosage forms in separate actions. The two administration actions may, or may not, be linked by a specified time interval. For example, administering Compound A and administering a PD-1 or PD-L1 inhibitor over a specified time such as once every 14 to 21 days.

The phrase "in combination with" includes the simultaneous, separate, and sequential administration of each of Compound A and a PD-1 or PD-L1 inhibitor to a cancer patient in need of treatment, particularly a colorectal cancer patient.

The term "co-administration" or "combined administration" encompasses the administration of the therapeutic agents to a single patient, and include treatment regimens in which the agents may be administered by different routes of administration or at different times.

The beneficial action of two therapeutic agents producing an effect in a single patient which is greater than the simple additive effects of each agent administered alone may be calculated, for example, using suitable methods known in the art such as the Sigmoid-Emax equation (Holford and Scheiner, *Clin. Pharmacokinet.*, 1981, 6: 429-453), the equation of Loewe additivity (Loewe and Muischenk, *Arch. Exp. Pathol. Pharmacol.*, 1926, 114: 313-326), the median-effect equation (Chou and Talalay, *Adv. Enzyme Regul.*, 1984, 22: 27-55), and the Bliss Independence method, or known equivalents. Each equation may be applied to experimental data to generate a corresponding graph to aid in assessing the effects of a drug combination as additive, within a biologically relevant range of additive, less than additive, or greater than additive.

The oncogenic role of Notch was first reported in human T-cell leukemia involving a translocation of the Notch1 intracellular domain to the T-cell receptor-β promoter region, resulting in the over expression of Notch1 intracellular domain (Grabher et al. *Nature Review Cancer,* 2006 (6):347-359; Weng et al. *Science*, 2004(306):269-271). Over expression of Notch1 intracellular domain in hematopoietic progenitor cells of mice caused the mice to exhibit T-cell acute lymphoblastic leukemia similar to humans. In addition to T-cell acute lymphoblastic leukemia; there is increasing evidence that Notch signals are oncogenic in other cancers through multiple mechanisms including receptor amplification and over expression of ligands and/or receptors including acute lymphoblastic leukemia, chronic lymphoblastic leukemia (Rosati et al, *Blood,* 2009(113): 856-865), acute myelogenous leukemia (Sliwa et al. *Int J Clin Exp Pathol,* 2014(7(3)): 882-889), chronic myelogenous leukemia (Nakahara et al. *Blood,* 2010(115(14)): 2872-2881), and erythroleukemia (Robert-Moreno et al, *Leukemia,* 2007(21): 1496-1503). Aberrant constitutive Notch signaling due to mutation or over expression of ligands and/or receptors is also implicated in a number of solid tumor malignancies including triple negative breast cancer (Stoeck et al, *Cancer Discovery,* 2014(4): 1154-1167), breast cancer, ovarian cancer (Park et al. *Cancer Research,* 2006(66):6312-6318), melanoma (Gast et al. *Genes, Chromosomes & Cancer,* 2010(49):733-745), lung cancer, non small cell lung cancer (Westhoff et al. PNAS, 2009(106):22293-22298), pancreatic cancer, glioblastoma, colorectal cancer, head and neck cancer, cervical cancer, prostate cancer, liver cancer, squamous cell carcinoma (oral), skin cancer and medulloblastoma (Rangathan et al., *Nature Review Cancer,* 2011(11):338-351 and Supplementary information S1 (table)). Aberrant constitutive Notch signaling due to mutation or over expression of ligands and/or receptors is also implicated in angiosarcoma (Ravi et al, *J Clin Oncol,* 2007, (25(18S, June 20 Supplement)): Abstract 10030), rhabdomyosarcoma (Belyea et al, *Clin Cancer Res,* 2011(17(23)): 7324-7336; Roma et al, *Clin Cancer Res,* 2011(17(3)): 505-513), liposarcoma (*J Clin Oncol,* 2009, (27(15S, Supplement)): Abstract 10526), malignant fibrous histiocytoma (Wang et al, *Cancer Res,* 2012, (72): 1013-1022), hepatocellular carcinoma (Villanueva et al, *Gastroenterology,* 2012, (143): 1660-1669), intrahepatic and extrahepatic cholangiocarcinoma (Wu et al, *Int J. Exp Pathol,* 2014, (7(6)): 3272-3279; Sekiya et al, *J Clin Invest,* 2012, (122(11)): 3914-3918; Yoon et al, *World J Gastroenterol,* 2011, (17(35)): 4023-4030), and adenoid cystic carcinoma (Bell et al, *Annals of Diagnostic Pathology,* 2014, (18): 10-13; Stoeck et al, *Cancer Discov,* 2014, (4): 1154-1167).

The nature of cancer is multifactorial. Under appropriate circumstances, therapeutic agents with different mechanisms of action may be combined. However, only considering a combination of therapeutic agents having different modes of action does not necessarily lead to combinations with advantageous effects. Specific therapeutic agents affording demonstrated beneficial effects (therapeutic effect such as enhanced efficacy and/or lower toxicity) compared with monotherapy of only one of the therapeutic agents is preferred.

The combination of the present invention is believed suitable for the treatment of T-cell acute lymphoblastic leukemia, acute lymphoblastic leukemia, chronic lymphoblastic leukemia, acute myelogenous leukemia, chronic myelogenous leukemia, erythroleukemia, triple negative breast cancer, breast cancer, ovarian cancer, melanoma, lung cancer, non small cell lung cancer, pancreatic cancer, glioblastoma, colorectal cancer, head and neck cancer, cervical cancer, prostate cancer, liver cancer, oral squamous cell carcinoma, skin cancer, medulloblastoma, hepatocellular carcinoma, intrahepatic and extrahepatic cholangiocarcinoma, desmoid tumor, soft tissue sarcoma, and adenoid cystic carcinoma, and particularly suitable for the treatment of soft tissue sarcoma patients, who have failed standard therapy. This includes patients having cancer showing resistance to monotherapy or showing resistance to combinations different from those of the present invention.

The terms "Complete Response" (CR), "Partial Response" (PR), "Progressive Disease" (PD), "Stable Disease" (SD), "Objective Response" (OR) are used consistent with definitions according to RECIST v1.1, Eisenhauer et al., *European Journal of Cancer,* 2009, 45, 228-247.

The term "time to disease progression" (TTP) refers to the time, generally measured in weeks or months, from the time of initial treatment, until the cancer progresses (see RECIST v1.1 definition for progressive disease) which is at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. The appearance of one or more new lesions is also considered progression. Such progression is evaluated by a skilled clinician.

The term "extending TTP" refers to increasing the time to disease progression in a treated patient relative to i) an untreated patient, or 11) a patient treated with less than both of Compound A and a PD-1 or PD-L1 inhibitor.

The term "survival" refers to the patient remaining alive, and includes overall survival as well as progression free survival.

The term, "overall survival" refers to the patient remaining alive for a defined period of time, such as 1 year, 5 years, etc. from the time of diagnosis or treatment.

The term, "progression free survival" refers to the patient remaining alive, without the cancer progressing.

As used herein, the term "extending survival" is meant increasing overall or progression free survival in a treated patient relative to i) an untreated patient, ii) a patient treated with less than both of Compound A and a PD-1 or PD-L1 inhibitor, or iii) a control treatment protocol. Survival is monitored for a defined period of time, such as one month, six months, 1 year, 5 years, or 10 years, etc., following the initiation of treatment or following the initial diagnosis of cancer.

The term "primary tumor" or "primary lesion" is meant the original cancer and not a metastatic tumor or lesion located in another tissue, organ, or location in the patient's body.

In one embodiment, the dose of Compound A is escalated until the Maximum Tolerated Dosage is reached, and a PD-1 or PD-L1 inhibitor of the present invention is administered with a fixed dose. Alternatively, Compound A may be administered in a fixed dose and the dose of a PD-1 or PD-L1 inhibitor may be escalated. Each patient may receive doses of Compound A and/or a PD-1 or PD-L1 inhibitor either daily or intermittently. The efficacy of the treatment may be determined in such studies, e.g., after 12, 18 or 24 weeks by evaluation of symptom scores every 6 weeks.

Compound A may be prepared by the procedures described in WO 2013/016081.

A PD-1 or PD-L1 inhibitor may be prepared by the procedures described in U.S. Pat. No. 8,008,449 and WO2006/121168; Hamid, O. et al., *New England Journal of Medicine*, 2013, 369 (2): 134-44; WO2009/114335, and U.S. Pat. Nos. 8,354,509; 8,609,089, US 2010028330, and/or US 20120114649; WO2010/077634; US2010203056; U.S. Pat. No. 7,943,743; US 20120039906; WO20111066389; WO2013/079174; and WO2007/005874; or by procedures well known and routinely used by one skilled in the art.

The following Examples illustrate the activity of each of Compound A alone, a PD-1 inhibitor alone, or a PD-L1 inhibitor alone, and the combination of Compound A and a PD-1 or PD-L1 inhibitor.

BIOLOGICAL EXAMPLE 1

In-vivo Study:

For in-vivo studies $1 \times 10^6$ CT26 cells (ATCC® CRL2639™) a colorectal cancer cell line, in 0.2 mL Hank's Balanced Salt Solution (HBSS) is implanted by subcutaneous injection in the hind leg of 6-8 weeks of age BALB/C female mice (Harlan Laboratories) Mice are fed ad libitum on normal chow. Treatment is initiated on day 6 of tumor implantation with oral administration (gavage) of Compound A in 1% Sodium carboxymethyl cellulose (Na-CMC) in 0.25% Tween® 80, or intraperitoneal injection of mouse anti PD-L1 antibody (10F.9G2, BioXcell Catalogue #: BE0101) in phosphate buffered saline (PBS) or intraperitoneal injection of mouse anti PD-1 (CD279) antibody (Clone: RMP1-14, BioXCell #: BP0146-R) in PBS or their respective vehicle in 0.2 mL volume. Compound A is administered at 8 mg/kg on a Monday, Wednesday and Friday schedule for 2 weeks and 10F.9G2 and RMP1-14 are administered at 250 µg/dose/animal on Monday and Thursday schedule for 2 weeks.

Tumor growth and body weight are monitored over time to evaluate efficacy and signs of toxicity. Bidimensional measurements of tumors are performed twice a week and tumor volumes are calculated based on the following formula: (Tumor Volume)=$[(L) \times (W2) \times (\Pi/6)]$ where L is mid-axis length and W is mid-axis width. Tumor volume data are transformed to a log scale to equalize variance across time and treatment groups. The log volume data are analyzed with a two-way repeated measures analysis of variance by time and treatment using the MIXED™ procedures in SAS™ software (version 8.2). The correlation model for the repeated measures is spatial power. Least squares means from the repeated measures analysis, anti-logged to the tumor volume scale, are shown in Table 1. P-values for comparing each pair of groups on study day 20 are shown in Table 2. Test Groups are:

1: 1% CMC/0.25° Tween® 80/0.05% Antifoam, Monday-Wednesday-Friday ×2, PO/PBS Monday-Thursday ×2, IP
2: Compound A, 8 mg/kg, Monday-Wednesday-Friday ×2, PO
3: Compound B (PD-L1), 250 µg/dose, Monday-Thursday ×2, IP
4: Compound C (PD-1), 250 µg/dose, Monday-Thursday ×2, IP
5: Compound A, 8 mg/kg, Monday-Wednesday-Friday ×2, PO/Compound B (PD-L1), 250 µg/dose, Monday-Thursday ×2, IP
6: Compound A, 8 mg/kg, Monday-Wednesday-Friday ×2, POI Compound C (PD-1), 250 µg/dose, Monday-Thursday ×2, IP Tumor growth and body weight are monitored over time to evaluate efficacy and signs of toxicity. Bidimensional measurements of tumors are performed twice a week and tumor volumes are calculated based on the following formula: (Tumor Volume)=$[(L) \times (W2) \times (\Pi/6)]$ where L is mid-axis length and W is mid-axis width. Tumor volume data are transformed to a log scale to equalize variance across time and treatment groups. The log volume data are analyzed with a two-way repeated measures analysis of variance by time and treatment using the MIXED™ procedures in SAS™ software (version 8.2). The correlation model for the repeated measures is spatial power. Treated groups are compared to the control group at each time point. The MIXED™ procedure is also used separately for each treatment group to calculate adjusted means and standard errors at each time point. Both analyses account for the autocorrelation within each animal and the loss of data that occurs when animals with large tumors are removed from the study early. The adjusted means and standard errors are plotted for each treatment group versus time. Antitumor activity is expressed as a tumor volume percentage for treatment versus control (% TIC) and is calculated by comparing tumor volume in the treatment group with vehicle treatment group. Percentage T/C and statistical significance value (p value) for the treatment groups is measured essentially as described above and summarized in Table 2.

TABLE 1

| | Tumor volume (mm³): Geometric Mean | | | | |
|---|---|---|---|---|---|
| | Study Days | | | | |
| Group | 8 | 10 | 14 | 17 | 20 |
| 1 Vehicle | 52.92 | 99.25 | 486.99 | 1045.42 | 1643.20 |
| 2 Compound A | 47.96 | 88.80 | 376.50 | 751.13 | 1227.40 |
| 3 Compound B | 49.82 | 96.48 | 378.49 | 790.67 | 1313.36 |
| 4 Compound C | 45.30 | 87.73 | 241.50 | 491.72 | 622.56 |
| 5 Compound A + B | 42.79 | 88.58 | 221.73 | 321.19 | 472.83 |
| 6 Compound A + C | 47.88 | 102.62 | 245.30 | 501.45 | 569.20 |

TABLE 2

| Group | Tumor volume all pairs comparison p value | | | | |
|---|---|---|---|---|---|
| | 2 Compound A | 3 Compound B | 4 Compound C | 5 Compound A + B | 6 Compound A + C |
| 1 Vehicle | 0.26 | 0.362 | <0.001 | <0.001 | <0.001 |
| 2 Compound A | | 0.828 | 0.009 | <0.001 | 0.001 |
| 3 Compound B | | | 0.005 | <0.001 | <0.001 |
| 4 Compound C | | | | 0.036 | 0.455 |
| 5 Compound A + B | | | | | 0.17 |

Table 2 shows the combination of Compound A and PD-L1 (Group 5), in this test, demonstrated statistically significant tumor growth inhibition results over each of Compound A (Group 2) and PD-L1 alone (Group 3). The combination of Compound A and PD-1 (Group 6) demonstrated statistically significant growth inhibition results over Compound A (Group 2) alone, but not over PD-1 (Group 4) alone.

Combination Analysis

Using the repeated measures analysis previously described, a contrast statement is used to test for an interaction effect on study day 20, using the two specific treatments (Compound A and PD-L1) that were combined. This test is statistically significant with p=0.008, demonstrating better than additive, or synergistic activity, since the estimated mean tumor volume in the combination group (298 mm$^3$) is less than the expected additive tumor volume per the Bliss Independence method (1134×1069/1448=837 mm$^3$).

Using the repeated measures analysis previously described, a contrast statement is used to test for an interaction effect on study day 20, using the two specific treatments (Compound A and PD-1) that were combined. This test is not statistically significant with p=0.769, demonstrating an additive effect, since the estimated mean tumor volume in the combination group (431 mm$^3$) is close to the expected additive tumor volume per the Bliss Independence method (526×1069/1448=389 mm$^3$).

Mechanism Analysis

For mechanism analysis CT-26 tumors are excised on day 20, 1h following the last dose of Compound A. A small piece of approximately 30 mg is cut and stored in RNALater for gene expression analysis. The remainder of the tumor is processed for the flow-cytometry analysis.

Flow-Cytometry

Tumors are weighed and then homogenized in 5 ml 4° C. complete media (CM; RPMI-1640/10% fetal bovine serum (FBS)) through 100 μm strainers to produce single-cell suspensions. Cells are centrifuged for 5 minutes at 466×g, 4° C.; the pellets are resuspended in fresh CM (0.5-3 ml, depending on pellet volume), and cells are counted using a Vi-Cell XR (Beckman Coulter). An equal number of total cells per tumor (10×10$^6$) are transferred to 96-well V-bottom microplates (Fisher Scientific). Cells are centrifuged (700× g, 3 min., 4° C.) and resuspended in 100 μl 1 μg/ml Fc block in CM (anti-CD16/32 (clone 2.4G2); Tonbo Biosciences) for 30 minutes on ice. Cells are centrifuged (700×g, 3 minutes, 4° C.) and resuspended in 100 μl of one of several flu-ochrome-conjugated surface marker antibody cocktails [anti-CD3 (clone 145-2C11), -Ly-6G (clone 1A8), -CD11c (clone HL3), -CD45 (clone 30-F11) (BD Biosciences), anti-CD8 (clone 53-6.7) (Biolegend), -CD11 b (clone M1/70), -CD3 (clone 145-2C11), -F4/80 (clone BM8), -CD4 (clone RM4-5), (eBioscience)] containing a fixable viability dye (eBioscience) and incubated for 30 minutes on ice covered from light. Cells are twice washed with 200 μl CM and centrifuged (700×g, 3 min., 4° C.). Following the second wash, cells are fixed, permeabilized, and intracellularly stained for Ki67 (clone SolA15) (eBioscience) using the Foxp3/Transcription Factor Staining Buffer Set (eBioscience), following the manufacturer's instructions with noted modifications. Briefly, cells are fixed in 100 μl/well for 30 min., followed by 100 μl/well permeabilization buffer with or without intracellular stain (depending on the staining panel used) for 30 min. Cells are twice washed with 200 μl 1× permeabilization buffer and centrifuged (700×g, 3 min., 4° C.), followed by resuspension in PBS with 2% FBS. 1×10$^6$ events, excluding debris, are captured for each sample using a 10-channel LSR II cytometer (BD Biosciences) and analyzed using FlowJo V.10.0.8 software. Data is represented as percent of tumor cells, with noted exceptions where represented as percent of parent population. Post-hoc t-test following ANOVA is used for statistical analysis between vehicle and treatment groups. The results are summarized in the Table 3.

TABLE 3

| Population | Vehicle | | Compound A | | Compound B PD-L1 (10F.9G2) | |
|---|---|---|---|---|---|---|
| | Mean % ± SEM | p value | Mean % ± SEM | p value | Mean % ± SEM | p value |
| CD4+/Ki67+ (% of CD4+) | 5.7 ± 0.9 | n.s. | 7.6 ± 0.5 | n.s. | 8.8 ± 1.2 | 0.022 |
| CD8+/Ki67+ (% of CD8+) | 21.8 ± 3.6 | n.s. | 23.1 ± 2.0 | n.s. | 24.1 ± 1.9 | n.s. |
| CD11b+ (% of Tumor) | 1.8 ± 0.2 | n.s. | 2.9 ± 0.2 | 0.002 | 2.1 ± 0.2 | n.s. |
| CD11b+F4/80+ (% of Tumor) | 0.62 ± 0.11 | n.s. | 0.89 ± 0.15 | — | 0.67 ± 0.07 | n.s. |
| CD11c+ (% of Tumor) | 0.24 ± 0.04 | n.s. | 0.42 ± 0.06 | 0.035 | 0.27 ± 0.03 | n.s. |
| CD11b+Ly-6G+F4/80− (% of Tumor) | 0.61 ± 0.08 | n.s. | 1.12 ± 0.08 | <0.001 | 0.76 ± 0.07 | n.s. |

TABLE 3-continued

| | Compound C PD-1 (RMPI-14) | | Compound A + PD-L1 (10F.9G2) | | Compound A + PD-1 (RMP1-14) | |
|---|---|---|---|---|---|---|
| Population | Mean % ± SEM | p value | Mean % ± SEM | p value | Mean % ± SEM | p value |
| CD4+/Ki67+ (% of CD4+) | 13.7 ± 2.0 | <0.001 | 14.1 ± 1.2 | <0.001 | 16.3 ± 1.4 | <0.001 |
| CD8+/Ki67+ (% of CD8+) | 32.1 ± 4.0 | 0.017 | 31.5 ± 1.2 | 0.005 | 34.4 ± 2.5 | 0.002 |
| CD11b+ (% of Tumor) | 3.9 ± 0.3 | <0.001 | 4.4 ± 0.5 | <0.001 | 4.2 ± 0.6 | <0.001 |
| CD11b+F4/80+ (% of Tumor) | 1.87 ± 0.18 | <0.001 | 1.75 ± 0.28 | <0.001 | 1.77 ± 0.33 | <0.001 |
| CD11c+ (% of Tumor) | 0.31 ± 0.05 | n.s. | 0.46 ± 0.08 | 0.039 | 0.32 ± 0.07 | n.s. |
| CD11b+Ly-6G+F4/80− (% of Tumor) | 0.99 ± 0.10 | 0.003 | 1.29 ± 0.16 | <0.001 | 1.29 ± 0.19 | <0.001 |

The data in Table 3 shows elevated inflammatory response as demonstrated by intra-tumoral CD4+Ki67+ (activated CD4+ T-cells), CD8+Ki67+ (activated CD8+ T-cells), CD11b+ (myeloid cells), CD11b+F4/80+ (macrophages), CD11c+ (Dendritic cells), and CD11b+Ly-6G+F4/80− (Neutrophils).

Gene Expression Analysis

For RNA isolation from the tumor, approximately 30 mg tissue is cut. RNA is extracted by RNeasy Protocol (version January 2002) using RNeasy 96-well Column Plates (Qiagen, Valencia, Calif.; Cat #74182) and QiaVac 96 vacuum manifold at 15 psi vacuum. Briefly, tissues are homogenized in 800 μL Buffer-RLT containing 1% β-mercaptoethanol in 2 mL Lysing Matrix-D® tubes (MP Biomedicals, Solon, Ohio; Cat #6913-500, Lot #6913-500-120156) in FP120 (ThermoFisher Scientific, Waltham, Mass.; Cat #6001-120) or FastPrep-24 (MP Biomedicals; Cat #116003500) at speed 6.0 for two mixings each of 30 seconds. Tubes are centrifuged at 14,000 revolutions per minute (RPM) for 30 minutes. Between 400-600 μL of supernatant is removed and mixed with equal volumes of 70% ethanol (Decon Labs, King of Prussia, Pa.; Cat #2401), and transferred onto 96-well RNeasy Plate. Any potential contaminating DNA is removed by additional DNase-I digestion (Qiagen, Cat #79254) on the column as per supplier's protocol. Total RNA is extracted in two 40 μL aliquots of DNase/RNase-free water. The total RNA concentration is estimated using Nanodrop ND-1000 spectrophotometer by absorbance at 260 nM (Thermo Scientific). Total RNA is stored at −80° C. until needed for cDNA synthesis.

The High Capacity cDNA Reverse Transcription Kit (Applied Biosystems, Framingham, Mass.; Cat #4368813) is used to reverse transcribe 3 μg total RNA in a final volume of 100 μL in 96-Well PCR Plates (Molecular Bioproducts, San Diego, Calif.; Cat #3419) using GeneAmp PCR System 9700 (Applied Biosystems) with following parameters: 25° C. for 10 minutes, 37° C. for 2 hours, and 4° C. for infinity. For long term storage, cDNA is stored at −30° C., and total RNA is stored at −80° C.

For Taqman procedure, 100 μL of cDNA is diluted with 200 μL RNase/DNase-free water in 96-Well Clear Optical Reaction Plate (Applied Biosystems, Cat #4306737) and transferred to 2 mL RNase/DNase-free tubes (Ambion, Cat # AM12475). Taqman reaction is carried out using 2× Universal Buffer (Applied Biosystems, Cat #4318157) in a final volume of 20 μL in 384-Well Clear Optical Reaction Plate (Applied Biosystems, Cat #4309849). Samples are dispensed with Tecan Automated Pipetting Workstation (Tecan US Inc., Durham, N.C.; Model: Freedom Evo-100 or Evo-150), and plates are read in ABI Prism 970011T SDS plate reader with following protocol settings: 50° C. for 2 minutes, 95° C. for 10 minutes, and 40 cycles at 95° C. for 15 seconds and 60° C. for 1 minute. The absolute $C_T$ values are normalized based on a standard curve-based method. All calculations are done in Microsoft Excel spreadsheet template, and % inhibition is calculated from control values. Statistical significance is analyzed on version 11 JMP Software (SAS, Cary, N.C.). The results are described in Table 4 as a fold change compared to vehicle control. Statistically significant values of >1.5-fold (1.5×) are shown. No significant change in the expression of genes examined in Compound A and PD-L1 alone treatment groups. The data demonstrates increased expression of genes associated with intra-tumoral inflammation and T-cell activation when Compound A is combined with PD-L1 or PD1 antibody. All Taqman primers and probes listed below were purchased from Applied Biosystems Inc. (AM) and their catalogue number listed in the table as ABI # along with summary of the results.

TABLE 4

| Gene | PD-L1 + Compound A | PD1 | PD1 + Compound A | ABI # |
|---|---|---|---|---|
| Ccl2 | | 1.5x | | Mm00441242_m1 |
| Ccl3 | | 2.4x | | Mm00441259_g1 |
| Ccl4 | | 2.4x | | Mm00443111_m1 |
| Ccl5 | 6.5x | 4.1x | 4.6x | Mm01302427_m1 |
| Infγ | 4.6x | 4.8x | 4.4x | Mm01168134_m1 |
| Il2 | 6.6x | 3.5x | 4.1x | Mm00434256_m1 |
| Il4 | 5.9x | 2.6x | 4.1x | Mm00445259_m1 |
| Il5 | 2.4x | | | Mm00439646_m1 |
| Il10 | | 2.0x | | Mm01288386_m1 |
| Il12b | 2.9x | 2.1x | | Mm01288989_m1 |
| Il13 | 11.2x | 5.0x | 8.0x | Mm00434204_m1 |
| Tnfα | 2.6x | 2.2x | | Mm00443260_g1 |
| Gzmb | 2.0x | 2.3x | 2.3x | Mm00442834_m1 |
| Tgfbr1 | | | 1.2x | Mm00436964_m1 |
| Tgfbr2 | 2.4x | | | Mm03024091_m1 |
| Pd-l1 | 3.2x | 2.7x | 3.2x | Mm00452054_m1 |
| Pd-l2 | 11.0x | 7.1x | 6.8x | Mm00451734_m1 |
| Pd-1 | 2.9x | 3.5x | | Mm01285676_m1 |
| Arg | 2.1x | | | Mm00477592_m1 |
| iNos | 5.8x | 4.7x | 5.9x | Mm00440502_m1 |

TABLE 4-continued

| Gene | PD-L1 + Compound A | PD1 | PD1 + Compound A | ABI # |
|---|---|---|---|---|
| Ido | 4.6x | 3.5x | 4.9x | Mm00492590_m1 |
| Icam | 2.5x | 2.0x | 1.9x | Mm00516023_m1 |
| Cd3e | | 3.2x | | Mm01179194_m1 |
| Cd4 | 3.1x | 2.6x | | Mm00442754_m1 |
| Cd8b1 | 3.2x | 3.3x | | Mm00438116_m1 |
| Cd20 | 8.9x | | | Mm00545909_m1 |
| Cd45 | | 1.7x | | Mm01293577_m1 |
| Cd68 | 1.6x | | 1.6x | Mm03047343_m1 |
| Cd69 | 1.8x | 1.7x | | Mm01183378_m1 |
| Cd86 | 2.0x | 1.6x | | Mm00444543_m1 |
| Foxp3 | 2.8x | 2.1x | 2.4x | Mm00475162_m1 |
| Icos | 4.0x | 2.7x | 2.8x | Mm00497600_m1 |
| Lag3 | 2.9x | 2.7x | | Mm00493071_m1 |
| Tim3 | 2.3x | 2.2x | 2.1x | Mm00454540_m1 |
| Tim4 | | 2.8x | 2.3x | Mm00724709_m1 |
| Cd40l | 4.3x | 2.7x | 2.8x | Mm00441911_m1 |
| Cd200r1 | 2.1x | 1.8x | 1.7x | Mm00491164_m1 |
| Tnfsf4(Ox40l) | 1.8x | | 2.0x | Mm00437214_m1 |
| Tnfsf18(Gitrl) | 2.2x | | 1.9x | Mm00839222_m1 |
| Tnfrsf4(Ox40) | 2.2x | 1.7x | 1.6x | Mm00442039_m1 |
| Tnfrsf18(Gitr) | 2.5x | 2.2x | 2.0x | Mm00437136_m1 |

We claim:

1. A method of treating colorectal cancer, comprising administering to a patient in need of treatment of colorectal cancer an effective amount of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof, and an effective amount of a PD-1 or PD-L1 inhibitor selected from pembrolizumab, nivolumab, atezolizumab, durvalumab, and avelumab.

2. The method of claim 1, wherein between 2.5 mg and 75 mg of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is administered.

3. The method of claim 1, wherein between 10 mg and 50 mg of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is administered.

4. The method of claim 2, wherein 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is administered once per day every other day over a five day period followed by two days without administration (T.I.W.).

5. The method of claim 1, wherein between 1 mg/kg and 3 mg/kg of the PD-1 or PD-L1 inhibitor is administered.

6. The method of claim 5, wherein the PD-1 or PD-L1 inhibitor is administered once every 14 to 21 days.

7. The method of claim 1, wherein between 2.5 mg and 75 mg of 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is administered, and between 1 mg/kg and 3 mg/kg of the PD-1 or PD-L1 inhibitor is administered.

8. The method of claim 7, wherein 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is administered once per day every other day over a five day period followed by two days without administration (T.I.W.), and the PD-1 or PD-L1 inhibitor is administered once every 14 to 21 days.

9. The method of claim 1, wherein 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide, or a pharmaceutically acceptable salt or hydrate thereof is administered orally, and the PD-1 or PD-L1 inhibitor is administered intravenously.

* * * * *